(12) United States Patent
De Lorenzo et al.

(10) Patent No.: US 8,381,593 B2
(45) Date of Patent: Feb. 26, 2013

(54) METHOD FOR THE REMOTE DETECTION, LOCALIZATION AND MONITORING OF CRITICAL FAULTS IN PIPELINES

(75) Inventors: Gianpietro De Lorenzo, Segrate (IT); Giuseppe Giunta, San Donato Milanese (IT); Alfredo Montini, Segrate (IT)

(73) Assignee: ENI S.p.A., Rome (IT)

( * ) Notice: Subject to any disclaimer, the term of this patent is extended or adjusted under 35 U.S.C. 154(b) by 208 days.

(21) Appl. No.: 12/988,751

(22) PCT Filed: Apr. 9, 2009

(86) PCT No.: PCT/EP2009/002776
§ 371 (c)(1),
(2), (4) Date: Jan. 4, 2011

(87) PCT Pub. No.: WO2009/129959
PCT Pub. Date: Oct. 29, 2009

(65) Prior Publication Data
US 2011/0114412 A1  May 19, 2011

(30) Foreign Application Priority Data

Apr. 24, 2008 (IT) .............................. MI2008A0759

(51) Int. Cl.
*G01N 29/14* (2006.01)
(52) U.S. Cl. ............................... 73/620; 73/587; 73/649
(58) Field of Classification Search ............... 73/620, 73/40.5 A, 587, 592, 600, 602, 649; 702/39, 702/56
See application file for complete search history.

(56) References Cited

U.S. PATENT DOCUMENTS

| | | | |
|---|---|---|---|
| 4,352,167 A | | 9/1982 | Hashimoto et al. |
| 4,450,711 A * | | 5/1984 | Claude ........................ 73/40.5 R |
| 4,641,526 A | | 2/1987 | Izumi et al. |
| 5,115,681 A | | 5/1992 | Bouheraoua et al. |
| 5,127,267 A * | | 7/1992 | Huebler et al. ................... 73/584 |
| 6,065,342 A * | | 5/2000 | Kerr et al. ........................ 73/587 |
| 6,728,662 B2 * | | 4/2004 | Frost et al. ..................... 702/188 |
| 8,060,319 B2 * | | 11/2011 | Stothers et al. .................. 702/39 |
| 8,087,311 B2 * | | 1/2012 | Merlo ........................... 73/865.8 |
| 8,228,078 B2 * | | 7/2012 | Herraez et al. ................. 324/705 |

FOREIGN PATENT DOCUMENTS

WO  98 57166  12/1998

OTHER PUBLICATIONS

International Search Report issued Sep. 2, 2009 in PCT/EP09/02776 filed Apr. 9, 2009.

\* cited by examiner

*Primary Examiner* — J M Saint Surin
(74) *Attorney, Agent, or Firm* — Oblon, Spivak, McClelland, Maier & Neustadt, L.L.P.

(57) ABSTRACT

With a certain pipeline, either underground or deposited on a sea/lake bottom, the formation of critical faults is determined and localized, which arise in the walls of the pipeline, or the growth of an already localized fault is monitored, through a method which detects, by acoustic sensors regularly distributed along the pipeline, the ultrasounds diffused along the walls of the pipeline itself upon the formation of a critical fault, or when a controlled fault increases, and processing, by a remote processor, the digital signals associated with the sound waves to identify the position or evaluate the development of a critical fault.

5 Claims, 4 Drawing Sheets

Velocity distribution of the transmission phenomenon of acoustic waves with the distance from the emission point.

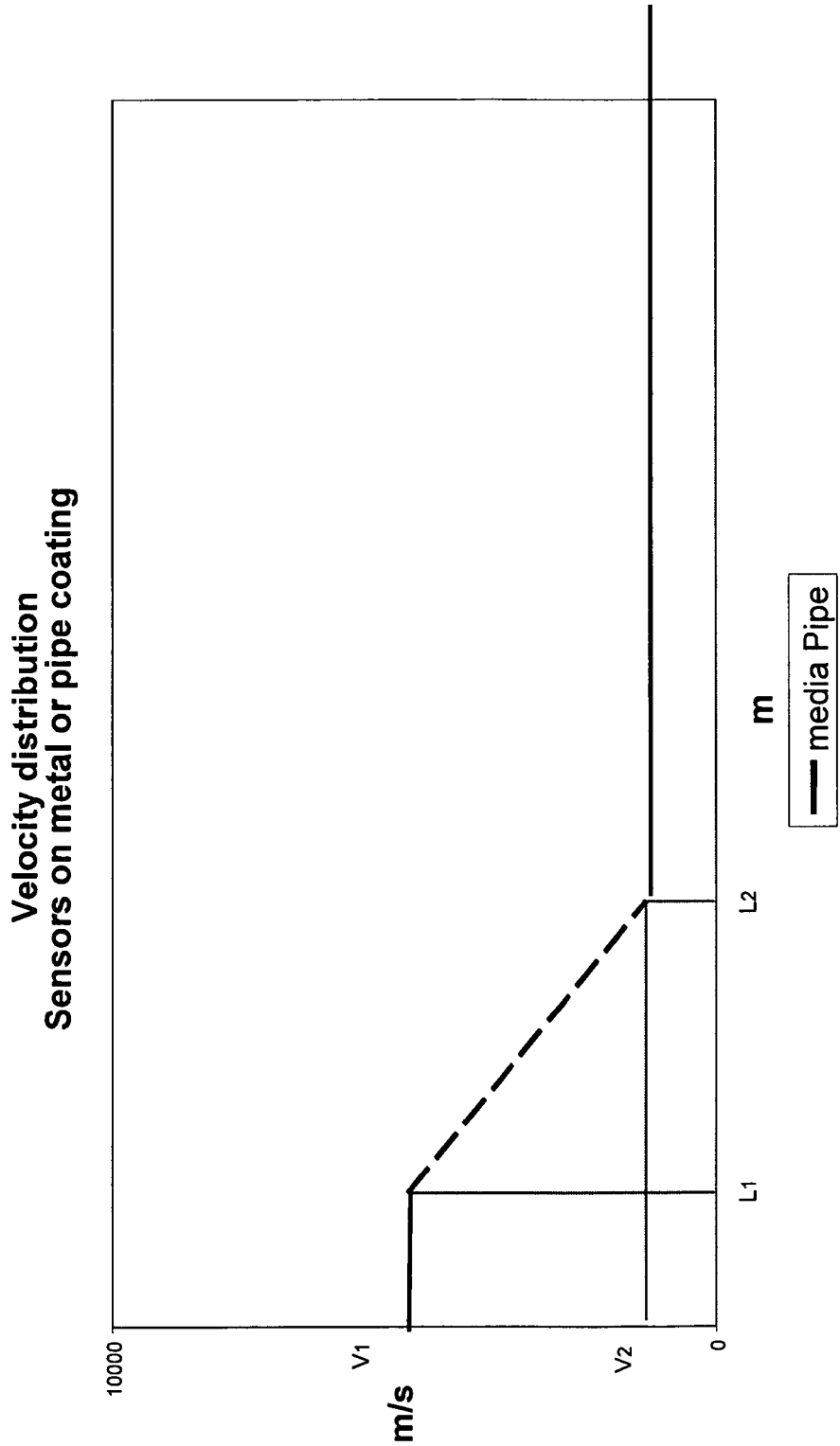
Fig. 1 Velocity distribution of the transmission phenomenon of acoustic waves with the distance from the emission point.

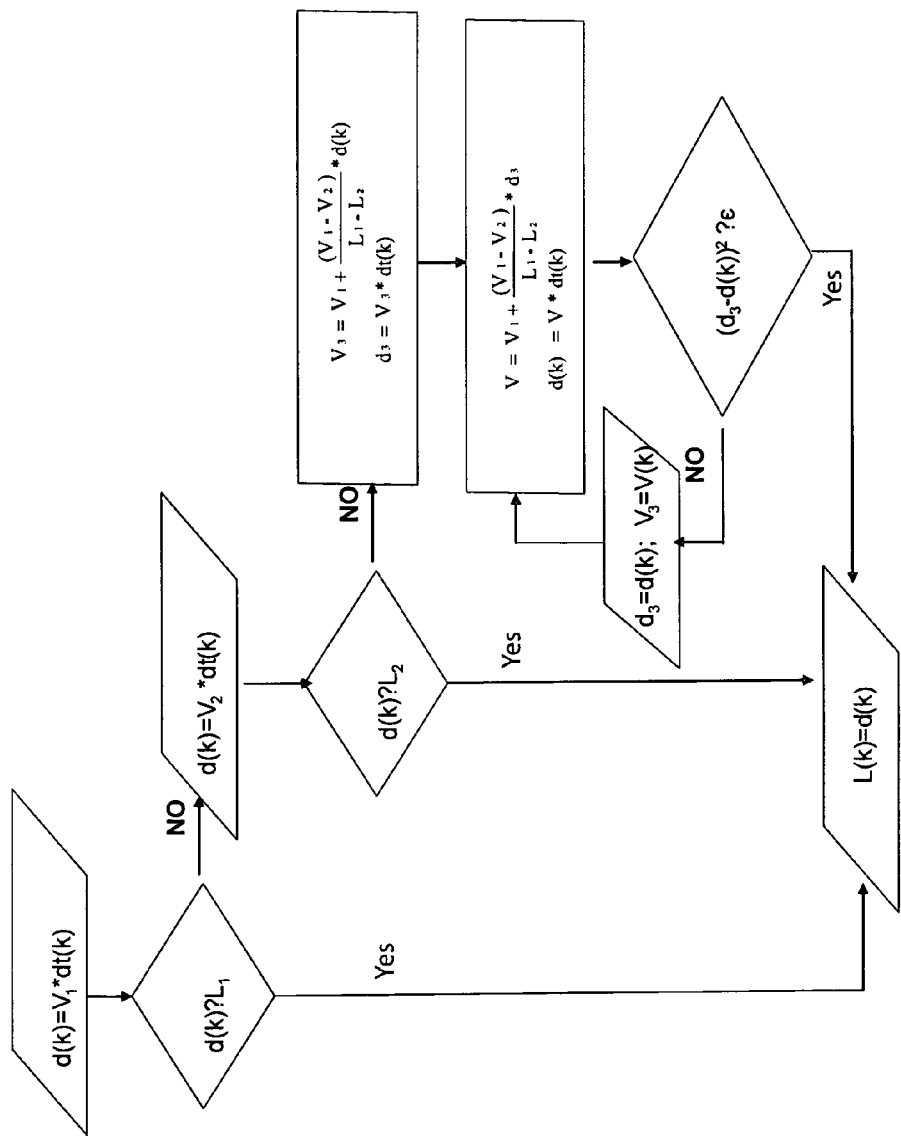
Fig. 2 Calculation scheme of the distance of a fault, L(k) from the sensor n°k.

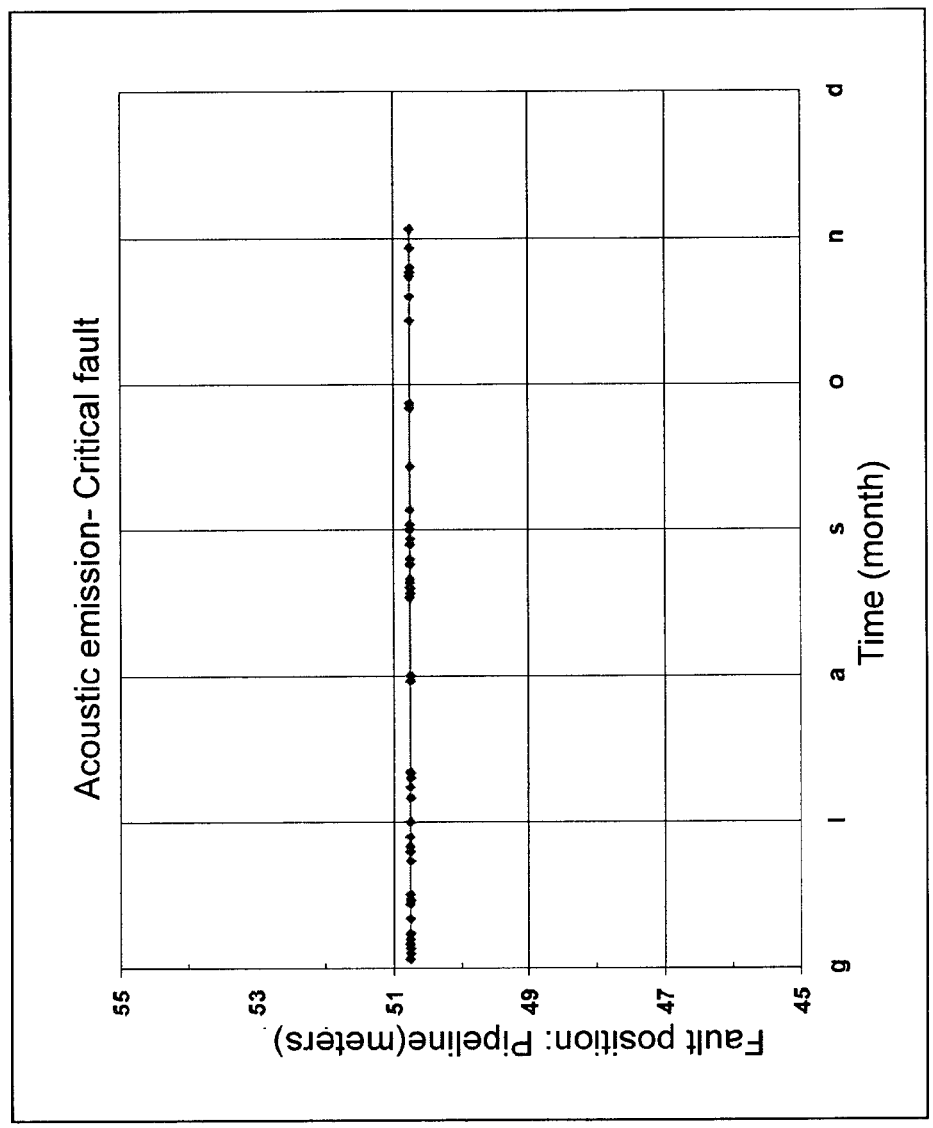
Fig. 3a  Acoustic emission graph with localization of the fault on the pipeline

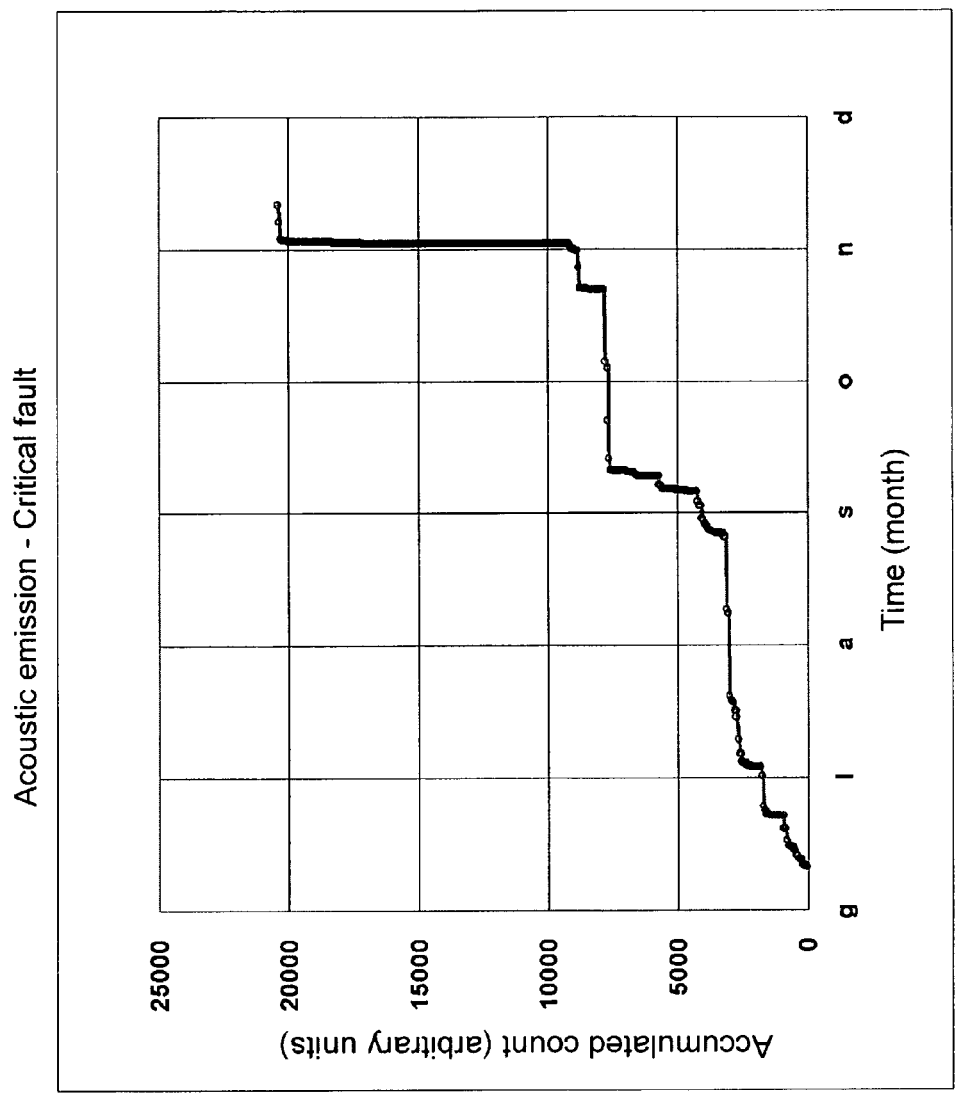
Fig. 3b  Acoustic emission graph of the fault with accumulation with time

METHOD FOR THE REMOTE DETECTION, LOCALIZATION AND MONITORING OF CRITICAL FAULTS IN PIPELINES

The present invention relates to a method for the remote detection, localization and monitoring of critical faults in pipelines.

More specifically, the present invention relates to a method for the remote detection, localization and monitoring of critical faults in pipelines either underground or sealines suitable for transporting gas or hydrocarbon liquids, such as natural gas (methane), petroleum or hydrocarbon derivatives of petroleum or water, fresh or salt water, particularly well production water.

Even more specifically, the present invention relates to a method for the remote monitoring of the structural integrity of gas ducts/oil ducts (pipelines) by the detection of acoustic emissions due to the formation of faults in the pipeline, the linear localization of the fault on the same and monitoring with time to control the development of the faults thus identified.

As is known, the transportation of fluids of a fossil nature, such as natural gas or petroleum, by means of pipelines is the simplest and most economical mode of transportation as it guarantees a continuous flow of the fluid, without substantial interruptions, from the production sites to the consumption/work areas or shipment areas for oversea transportation.

As mentioned above, the transportation of these products through pipelines is only substantially continuous because, for maintenance purposes, the pipelines must be periodically controlled. In other words, as the pipelines are subject to mechanical stress, the flow of fluid is periodically interrupted, or substantially reduced, to allow the operators to introduce suitable devices inside the pipeline for detecting the possible formation of critical faults (for example cracks or corrosion points) and monitoring the development of those previously detected.

These operations for controlling and monitoring of critical faults are fundamental for correctly managing the pipeline as they enable to carry out the interventions and repairs on the fault before it causes greater damage to the pipeline.

The risk of the crack formation in the material of a pipeline, generally carbon steel, is due to reasons associated with the fluid transported and also to external causes. In the former case, the risk factor is linked to the pressure jumps of the fluid transported which cause radial expansions and contractions of the pipe which, with time, can cause the formation of faults due to fatigue stress. In the latter case, as the pipeline is underground or resting on sea/lake bottoms, these are subject to movement of the earth or sea currents which tend to deform them.

The control and monitoring system of pipelines currently in use has at least one evident drawback, in addition to that previously mentioned with respect to the necessity of interrupting or reducing the flow of fluid transported to allow the introduction and subsequent recovery of control devices. If, in fact, the presence of a fault in the material of the pipeline being examined is discovered, by means of these control devices, this can and will have to be monitored discontinuously, periodically, with the relative stoppages/reductions in the flow of fluid transported inside the pipeline.

An objective of the present invention is to provide a method for the detection, localization and monitoring of critical faults in underground and underwater pipelines, suitable for transporting gas or hydrocarbon liquids, such as for example, natural gas (methane), petroleum or hydrocarbon derivatives of petroleum, well-production water, etc., which does not have the drawbacks mentioned above and allows the formation of a critical fault to be identified at the moment of its formation, with the continuous monitoring of the possible development of the fault, without intervening on the flow-rate of the fluid transported. In this way, an operator can repair the section of pipeline involved when the fault has become such as to endanger the integrity of the pipeline itself. In particular, the method developed takes into consideration some important factors such as the characteristics of the pipeline and the materials used, indicating, in the calculation for the localization of the fault, two or more propagation rate ranges which vary with a variation in the relative distance between the fault-source and the acoustic sensors installed on the pipeline.

An object of the present invention therefore relates to a method for the remote detection, localization and monitoring of critical faults in underground or underwater pipelines, which comprises:

a. arranging, on the outer surface of the pipeline, a first plurality of passive acoustic sensors (passive acoustic transducers) capable of detecting the emission of sound waves within the range of ultrasounds;

b. detecting, by means of said passive acoustic sensors, the sound waves (ultrasounds) distributed along the walls of the pipeline with the formation of a critical fault or at the moment of a development of a fault already under control;

c. transforming the signals received into electric signals;

d. transmitting the electric signals coming from the at least two passive sensors closest to the critical fault, positioned near said fault, to a data collection centre;

e. transforming each electric signal received into a digital signal sent to a remote processor system, equipped with software, which identifies the reception time of the signal emitted from the fault, relating to said at least two passive sensors close to the fault, by a measurement of the sound intensity of the emission;

f. identifying and/or monitoring, by means of software, the relative position of the fault that has arisen or that is developing, with respect to said at least two passive sensors which have revealed the sound emission and its distance L(k) from said at least two passive sensors, starting from that furthest away from the fault, by the development of the equation:

$$L(k) = V_k(s, \tau) \times t$$

wherein $V_k(s,\tau)$ is the propagation velocity of the sound waves relating to the sensor k of said at least two passive sensors, depending on the space (s) that the sound waves must cross through the physical means of the pipeline, the propagation time (t) and the time ($\tau$) depending on the service state of the sensor k.

The term "service state of the sensor" as used in the present description and in the claims refers to a measurement of the receptive function of the passive sensors which is in relation to the service time and work conditions.

A more complete appreciation of the invention and many of the attendant advantages thereof will be readily obtained as the same becomes better understood by reference to the following detailed description when considered in connection with the accompanying drawings, wherein:

FIG. 1 is a velocity distribution of a transmission phenomenon of acoustic waves with a distance from an emission point;

FIG. 2 is a calculation scheme of a distance of a fault from a sensor; FIG. 3a is an acoustic emission graph with localization of a fault on a pipeline; and FIG. 3b is an acoustic emission graph of a fault with an accumulation of time.

One or more active acoustic sensors (active acoustic transducers), distributed along the outer surface of the pipeline, can be used for the purpose, which are capable of emitting, on command, ultrasounds that are comparable with those emitted from a real fault which is formed "ab initio" in the pipeline or which are emitted from a fault already present in the pipeline and which evolves with time. In this way, the periodical activation of said active sensors not only allows the service state of the passive sensors to be controlled, but also allows the periodical calibration of the whole monitoring system, object of the present invention.

According to the present invention, the identification of the formation of a critical fault or the monitoring of a pre-existing fault can be effected on any type of pipeline even if it is preferable to apply the method, object of the present invention, on underground pipelines or pipelines deposited on sea/lake bottoms, as, once functioning, they are only accessible with programmed recovery and maintenance interventions. Examples of pipes are those made of carbon steel with diameters of up to 150 cm, for example from 10 to 130 cm, possibly coated with protective materials of a plastic nature fixed to the metal by thermowelding or by hot-melt adhesives.

The acoustic sensors can be arranged over the whole length of the pipeline at predefined intervals. For economical reasons, however, it is preferable to arrange them in correspondence with potentially critical sections such as weldings, curves, sections subject to stress due to the ground movement, etc. Once the potentially critical sections have been identified, the sensors are generally arranged over lengths of 800-1,500 m of pipeline, at distances from each other of 10 to 50 m preferably from 20 to 40 m, generally at a distance of 30 m.

The sensors can be arranged in a straight line on the section of pipeline of interest, along a generating linea or around a pipeline according to a substantially helicoidal line. Alternatively, the sensors can be arranged around each of a plurality of fixed positions spaced linearly from each other.

The distance between each sensor is preferably always the same, then the software takes into account the distances between the sensors for processing the signals.

Any acoustic sensor capable of detecting the diffusion of sound waves (ultrasounds) on steel pipes, possibly coated with protective material of a plastic nature, can be used in the method, object of the present invention, even if acoustic sensors of the piezoelectric type are preferred as they are selective for that range of sound frequencies (30-600 kHz).

Alternative acoustic sensors can be electromagnetic transducers or "magnetostrictive" transducers.

The propagation rate of the sound wave resulting from the formation of a critical fault on the pipeline, or from the development of a fault under control, depends on the position in which it is formed, whether superficially, outside the pipeline or inside the pipeline, or in the thickness of the pipe. In any case, the propagation velocity is influenced by the materials, generally by the protection material of the pipeline (in the case of a fault on the outer surface) or by the fluid transported (in the case of a fault on the inner surface). The signals received at least from a first closer sensor and from at least a second more distant sensor, transformed into electric signals in situ, are transmitted to a data collection centre, transformed into digital signals and remotely sent where a process unit processes them to identify their origin, particularly if on the right or left of said at least a first closer sensor and the distance from said at least second more distant sensor.

Once the positions of the sensors along the pipeline and its geometrical characteristics are known, the software effects the following operations:

1. calculation of the position of the fault;
2. historical analysis of the dependence of the emission of a fault on forcing actions, such as operative cycles of temperature, pressure, flow, corrosion, etc. and on the time in general; and
3. calibration of the detection system.

In particular, with each detection cycle, the software allows the determination of the position of the fault and the definition of the statistic relations for its monitoring:

between the intensity of the acoustic emission and the emission frequency per fault;

between the acoustic emission times and the number of emission hits per fault;

between the values of acoustic emission hits per fault and the values of the local parameters of temperature, pressure, flow, precipitation of salts, etc.

between the acoustic emission frequencies per fault and the values of the local parameters of temperature, pressure, flow, precipitation of salts, etc.

between the parameters which define the form of the acoustic signal detected, also called in technical terminology: rise time, peak time, duration time, etc. and the local parameters of temperature, pressure, flow, precipitation of salts, etc.

between the parameters which define the form of the acoustic signal detected, as described above, and the local parameters of temperature, pressure, flow, precipitation of salts, etc.

between the parameters which define the form of the acoustic signal detected, as described above, and the frequencies and times of the emission events, per fault.

The calculation of the position of a fault is the main action of the software. This depends on the definition, in an acoustic sense, of the materials which form the pipeline or which flow through it.

A material is generally characterized by two parameters: the acoustic velocity and the acoustic attenuation. The former is the propagation velocity of the elastic waves and is calculated from the measured propagation time, also called time of flight, or it is the time necessary for the sound to go through a certain dimension of the material. The second is a measurement of the loss of energy of the sound wave.

The acoustic velocity v, and the attenuation coefficient, $\alpha$, are determined by measuring the time between two successive echoes (time of flight) and their relative amplitudes according to the formulae:

$$v = h/t \text{ [m/s]}$$

$$\alpha = (h)^{-1} * 20 \log_{10}(A1/A0) \text{ [dB/metre]}$$

wherein h is the distance between the fault and the active sensors or passive sensors, A0 and A1 are the amplitudes of the two echoes and t is the flight time calculated as the difference $t = t1 - t0$.

In the analysis of an acoustic beam, it is possible to distinguish two areas, called near field and far field. The near field is the region of space where the transmission velocity resulting from the advancing of the sound wave is characterized by a maximum transmission value, $V_1$. The acoustic pressure of the emission is dampened as the emission point moves away from the acoustic sensor. The far field is the area in which the acoustic pressure decreases up to a bottom plateau value characterized by a velocity $V_2$. FIG. 1 is a general representation of the transmission phenomenon.

FIG. 1 indicates, in the ordinate, the resulting values of the acoustic velocities calculated by means of passive sensors following the emissions, one at a time, of active sensors, during a calibration period. In the abscissa, the relative distance is indicated between the sensors in the calibration process. Curves are traced on the graph, which indicate the calculation functions of the velocity of the acoustic signal in the domain of the relative distances between the sensors.

A descriptive type of the velocity function of the acoustic signal in FIG. 1 requires a minimum of two average velocity transmission values, $V_1$ and $V_2$, valid in the distance fields between the emission point and the receiving sensor, for $x \leq L_1$ and for $x > L_2$, respectively.

An iterative calculation process scheme of the position of a fault, by means of the velocity distribution of FIG. 1, is indicated in FIG. 2. The scheme considers the case of an emission hit detected by two passive sensors, k=1, 2, wherein $x_1 \leq x_2$ ($x_1$ and $x_2$ represent the positions of two sensors along the pipeline and are the relative distances between the two sensors), with the sensor k=1 which detect the signal before k=2. In the process dt(k) is the time of flight of the acoustic signal detected by the sensor k and d(k) the position of the fault, relating to the sensor k, calculated with dt(k) and the velocity (V(k)) in FIG. 1, for k=1, ..., n.

The scheme in FIG. 2 represents a research process of the velocity of the transmission phenomenon based on the definition range of the velocity function described in FIG. 1. The scheme considers the following steps:
1. first calculation of the distance, d(k), between the fault and sensor k, the time of flight dt(k) at the sensor k being known, assuming the maximum transmission velocity $v_1$: d(k)=$V_1$*dt(k);
2. verification of the applicability of the rate $V_1$: if d(k)≤$L_i$ then the distance L(k) of the fault from the sensor k coincides with the distance d(k) calculated;
3. if the verification under point 2 is negative, a second calculation of the distance d, between fault and sensor k, is calculated, the flight time dt at the sensor k being known, assuming the minimum transmission velocity $v_2$: d(k)=$V_2$*dt(k);
4. verification of the applicability of the rate $V_2$: if d(k)≥$L_2$ then the distance L(k) of the fault from the sensor k coincides with the distance d(k) calculated;
5. if the verification under point 4 is negative, a second calculation of the velocity $V_3$(k) is effected, which characterizes for d(k) the intermediate transmission velocities between V1 and V2, in correspondence with L1 and L2:

$$V_3(k) = V_1 + \frac{(V_1 - V_2)}{L_1 - L_2} * d(k)$$

A new calculation of the distance $d_3$ is then effected, between the fault and sensor k, the time of flight dt at the sensor k being known, using the transmission velocity $V_3$(k): $d_3$=$V_3$(k)*dt(k);
6. a new calculation of the velocity V(k) is provided, which characterizes for $d_3$ the intermediate transmission velocities between V1 and V2:

$$V(k) = V_1 + \frac{(V_1 - V_2)}{L_1 - L_2} * d_3$$

The distance, d(k), between the fault and sensor k is then recalculated, the time of flight dt at the sensor k being known, using the transmission velocity V(k): d(k)=V(k)*dt(k);

7. verification of the convergence of the calculation and applicability of the velocity V(k): if $(d3-d(k))^2 \leq \epsilon$, $\epsilon$ being a small positive number as desired, then the distance L(k) of the fault from the sensor k coincides with the distance d(k) calculated;
8. if the verification under point 7 is negative, d3=d(k) e V3=V(k) is established, returning to point 6 to effect the calculation of the new velocity V(k) for the last distance d(k). The calculation cycle 6, 7 and 8 continues until the verification of point 7 or until a maximum number of recalculation cycles, Nc is reached, defined a priori, over which the average value of the last two distances calculated in the iterative process has been assumed.

The position of a fault detected by various sensors is obtained following a triangulation approach between "n" distances of the fault from the fixed positions of the "n" sensors which have revealed its emission event.

As illustrated above, various sensors are necessary for the present invention. Some of these, called active sensors, are used as sound wave sources for the calibration phase of the measurement process through passive sensors (receivers). The detections of the acoustic phenomenon induced in the calibration is therefore a complex function of material parameters through which the sound waves pass and, implicitly, of the specific set-up of the single sensor.

If m is the number of acoustic sensors with an active functionality and n the number of acoustic sensors with a passive functionality, the calibration process defines the transmission phenomenon between different positions along the pipeline. The application of the analysis process of the signal emitted from the j-th active sensor, for j=1, ..., m, and detected by "n" passive sensors, with m≤n, allows the transmission velocity of the acoustic wave to be determined and the attenuation of the acoustic signal in relation to cylindrical or Cartesian space coordinates on the surface of the pipeline.

If the "n" distribution functions of the velocities are $V_k(x_j)$, for k=1, n, relating to the positions $x_j$, for j=1, ..., m, of the calibration emission point, it is therefore possible to position the emission point or fault on the material of the pipeline during the acoustic monitoring process of the pipeline by means of an interpolation process.

The sensors can be applied on the pipeline according to any known method. It is preferable however to apply them on the pipeline through a specific method which comprises:
i. arranging a substantially rectangular steel supporting plate, having a pass-through opening, on the pipeline;
ii. supporting the acoustic sensor on the plate in correspondence with the pass-through opening, and the associated electronics;
iii. welding one of the two edges of the plate, orthogonal to the axis of the pipeline, onto the pipeline itself and holding the parallel sides, to the axis of the pipeline, of the supporting plate between two overturned L flanges welded onto the pipeline in correspondence with the other orthogonal edge;
iv. covering the acoustic sensor and the associated electronics with a protection box which adapts itself to the plate;
v. positioning a blocking spring between the acoustic sensor and the internal top of the box;
vi. fixing the covering box to the supporting plate.

The supporting plate can be rectangular or square and can have a pass-through opening wherein the acoustic sensor is inserted so that it can rest in contact with the metal or the coating of the pipeline. A spring is positioned above the sensor, in order to prevent the sensor from moving during the operation and, therefore, no longer having an adequate contact with the pipeline, so that when the box is inserted and is fixed to the supporting plate, the spring exerts, through the top of the box, a pressure force which acts on the acoustic sensor keeping it blocked in its original position. The covering box is fixed to the supporting plate by means of screws which are engaged in threaded holes present on the plate itself.

The top of the box can be integral, and not separable from the walls of the box or it can be extracted and fixed to the walls of the box by suitable fixing means, for example screws.

The plate is fixed to the pipeline, partially by welding and partially through the overturned L-shaped flanges shaped. The latter are situated (welded only on the outer surface of the pipeline) so as to keep the plate pressed against the pipe. This arrangement does not allow upward movements of the plate, but only longitudinal sliding movements which second the radial elastic deformations of the pipeline, in particular the radial elastic deformations due to the pressure jumps of the fluid transported.

According to an alternative method, step (iii), which constrains the supporting plate to the pipeline, can be different, with no welding of the edge and containment in correspondence with the other of the L-shaped flanges. In particular, the edges of the plates orthogonal to the axis of the pipeline can be shaped to respectively receive two belts which are tightened around the pipeline.

In order to avoid an extremely rigid fixing system, at least two spring elements are respectively positioned between the belt and each shaped part of the two edges of the plate, which allow the plate to follow the radial movements of the pipeline when subjected, for example, to the above radial deformations.

For safety reasons, in order to avoid damage to the acoustic sensor and/or the associated electronics, due to possible escape currents or electric discharges from atmospheric events, it is preferable for the belts not to be metallic but made of electrically non-conductive materials. Belts made of thermoplastic polymers, polyethylene or polypropylene, reinforced with glass and/or Kevlar® fibres, can be used for the purpose.

The present invention will be illustrated, for illustrative and non-limiting purposes, by the following practical example.

EXAMPLE

A carbon-steel pipe, covered by a 5 mm-thick coating of polyethylene, having a length of 250 m and a diameter of 120 cm, was buried at a depth of about 3 m, after modifying the external surface by a plurality of notches whose function was to simulate the presence of faults which are naturally formed in a real pipeline.

Before laying the pipeline, 20 sensors of the piezoelectric type were distributed on its external surface, at a distance of 10 m from each other. Electric wires extended from the sensors for the transportation of signals to a data collection centre situated close to the pipeline. The data collection centre transformed said electric signals into digital signals, which were analyzed and transmitted, through a GSM modem, to a remote data processor, at a distance of about 500 km from the pipeline.

Once it had been buried, the pipeline was filled with water at about 100 bar of pressure and then subjected to approximately 6,000 continuous pressure cycles in order to monitor the degenerative development of the notches. The test was carried out for about 24 months, until the degeneration of the notches caused the explosion of the pipeline.

In this respect, the result of a linear triangulation is shown, i.e. in one dimension, which uses the velocity distribution in FIG. 1.

FIG. 3a shows in the ordinate, the linear determination of the position of a fault on the pipeline over a period of time. FIG. 3b represents in the ordinate, the cumulated emission, over a period of time, coming from the fault (ordinate of FIG. 3a). The case refers to a known fault on the matrix of the pipeline.

The characteristic of a fault which grows with time is represented by an emission having small variations in the position on the pipeline, for ever-increasing emission values in the module during the monitoring time.

The invention claimed is:

1. A method for the remote detection, localization and monitoring of critical faults in underground or underwater pipelines, comprising:
   a. arranging, on the outer surface of the pipeline, a first plurality of passive acoustic sensors configured to detect the emission of acoustic waves within the range of ultrasounds;
   b. detecting, by means of said passive acoustic sensors, the acoustic waves (ultrasounds) distributed along the walls of the pipeline with the formation of a critical fault or at the moment of a development of a fault already under control;
   c. transforming the signals received into electric signals;
   d. transmitting the electric signals coming at least from the two passive sensors closest to the critical fault, positioned near said fault, to a data collection centre;
   e. transforming each electric signal received into a digital signal sent to a remote processor system, equipped with software, which identifies the reception time of the signal emitted from the fault, relating to said at least two passive sensors close to the fault, by a measurement of the acoustic intensity of the emission hit;
   f. identifying and/or monitoring, by means of software, the relative position of the fault that has arisen or that is developing, with respect to said at least two passive sensors which have revealed the sound emission and its distance L (k) from said at least two passive sensors, starting from that furthest away from the fault, by the development of the equation:

$$L(k) = V_k(s,\tau) \times t$$

wherein $V_k(s,\tau)$ is the propagation rate of the acoustic waves relating to the sensor k of said at least two passive sensors, depending on the space (s) that the sound waves must cross through the physical means of the pipeline, the propagation time (t) and the time ($\tau$) depending on the service state of the sensor k.

2. The method according to claim 1, wherein the passive sensors are positioned in correspondence with potentially critical piping tracts.

3. The method according to claim 1 wherein the passive sensors are arranged over a length of 800-1500 m of pipeline, at distances of 10 to 50 m from each other.

4. The method according to claim 1, wherein the passive sensors are of the piezoelectric type.

5. The method according to claim 1, wherein one or more active acoustic sensors are positioned on the outer surface of the pipeline, which are configured to emit, on command, acoustic waves (ultrasounds) comparable with those emitted by a real fault.

* * * * *